(12) United States Patent
Hanano et al.

(10) Patent No.: US 8,547,427 B2
(45) Date of Patent: Oct. 1, 2013

(54) ILLUMINATION DEVICE AND OBSERVATION SYSTEM

(75) Inventors: Kazunari Hanano, Tokyo (JP); Takeshi Suga, Tokyo (JP); Hirokazu Godo, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/613,803

(22) Filed: Sep. 13, 2012

(65) Prior Publication Data

US 2013/0113911 A1 May 9, 2013

Related U.S. Application Data

(63) Continuation of application No. PCT/JP2011/078236, filed on Dec. 7, 2011.

(30) Foreign Application Priority Data

Jan. 28, 2011 (JP) ................................. 2011-016945

(51) Int. Cl.
*H04N 9/47* (2006.01)
*H04N 7/18* (2006.01)

(52) U.S. Cl.
USPC .......................................................... 348/79

(58) Field of Classification Search
None
See application file for complete search history.

(56) References Cited

U.S. PATENT DOCUMENTS

| 7,497,581 | B2 * | 3/2009 | Beeson et al. | 362/84 |
| 7,656,520 | B2 * | 2/2010 | Cohn et al. | 356/237.2 |
| 7,660,035 | B2 * | 2/2010 | Bohm et al. | 359/385 |
| 2006/0203468 | A1 * | 9/2006 | Beeson et al. | 362/84 |
| 2011/0217665 | A1 * | 9/2011 | Walsh et al. | 433/29 |

FOREIGN PATENT DOCUMENTS

| JP | 7-56134 | 3/1995 |
| JP | 2005-250059 | 9/2005 |
| JP | 2008-176083 | 7/2008 |
| JP | 2008-292547 | 12/2008 |
| JP | 2009-86057 | 4/2009 |

OTHER PUBLICATIONS

International Search Report dated Mar. 13, 2012, issued in corresponding International Application No. PCT/JP2011/078236.

* cited by examiner

*Primary Examiner* — Nhon Diep
(74) *Attorney, Agent, or Firm* — Kenyon & Kenyon LLP

(57) ABSTRACT

An illumination device and an observation system capable of outputting light having a continuous spectrum and high color rendering properties are provided. Employed is an illumination device including a first light source that emits first-wavelength-band light having a first wavelength band of violet color; a second light source that emits second-wavelength-band light having a second wavelength band that is broader than the first wavelength band and having a continuous spectrum; a light combining section that is composed of a dicroic mirror and that combines the first-wavelength-band light and the second-wavelength-band light; and a combination-ratio adjusting section that adjusts the combination ratio of the first-wavelength-band light and the second-wavelength-band light to be combined by the light combining section.

7 Claims, 19 Drawing Sheets

ILLUMINATION DEVICE AND OBSERVATION SYSTEM

CROSS-REFERENCE TO RELATED APPLICATIONS

This is a continuation of International Application PCT/JP2011/078236, with an international filing date of Dec. 7, 2011, which is hereby incorporated by reference herein in its entirety. This application claims the benefit of Japanese Patent Application No. 2011-016945, the content of which is incorporated herein by reference.

TECHNICAL FIELD

The present invention relates to an illumination device and an observation system having the same.

BACKGROUND ART

There are conventionally known illumination devices in which a plurality of light sources are provided to emit light beams having different wavelength bands from each other, and the light beams having different wavelength bands emitted from the light sources are combined by a dichroic mirror and output (for example, see PTLs 1 to 3).

CITATION LIST

Patent Literature

{PTL 1} Japanese Unexamined Patent Application, Publication No. 2009-86057
{PTL 2} Japanese Unexamined Patent Application, Publication No. 2008-292547
{PTL 3} Japanese Unexamined Patent Application, Publication No. 2008-176083

SUMMARY OF INVENTION

Technical Problem

According to the illumination devices disclosed in PTLs 1 to 3, the dichroic mirror, which transmits light having a particular wavelength band and reflects light having wavelength bands other than the particular wavelength band, combines light beams having different wavelength bands; therefore, the combined light has a discontinuous spectrum.

Solution to Problem

A first aspect of the present invention provides an illumination device including: a first light source that emits first-wavelength-band light having a first wavelength band of violet color; a second light source that emits second-wavelength-band light having a second wavelength band that is broader than the first wavelength band and having a continuous spectrum; a light combining section that is composed of a dicroic mirror and that combines the first-wavelength-band light and the second-wavelength-band light; and a combination-ratio adjusting section that adjusts the combination ratio of the first-wavelength-band light and the second-wavelength-band light to be combined by the light combining section.

A second aspect of the present invention provides an observation system including: the above-described illumination device; and an imaging device that acquires an image of a specimen illuminated by the illumination device.

DESCRIPTION OF EMBODIMENTS

First Embodiment

An illumination device according to a first embodiment of the present invention will be described below with reference to the drawings.

Figure 1:
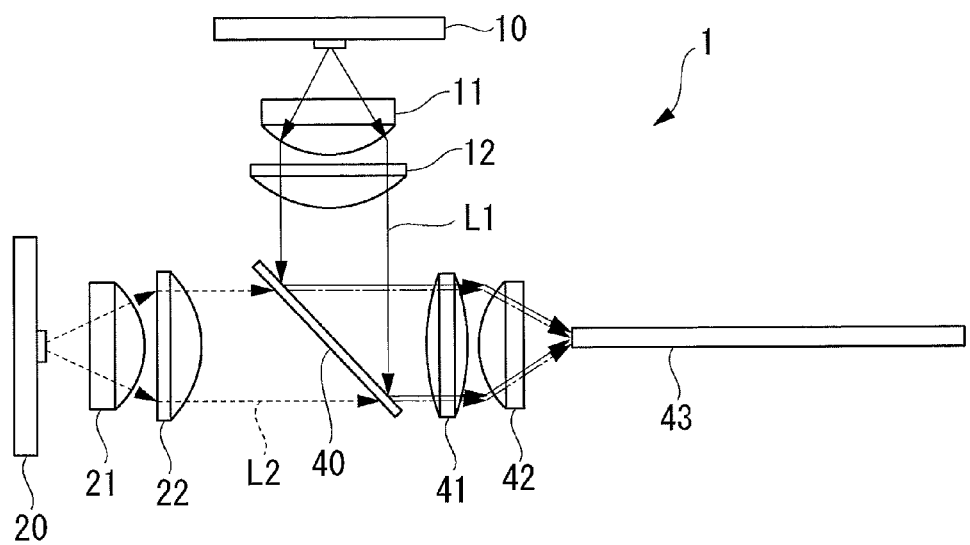
FIG. 1 is a view showing, in outline, the configuration of an illumination device according to a first embodiment of the present invention (NBI mode).

An illumination device 1 of this embodiment is applied to an observation system for observing body tissue, for example, and includes, as shown in FIG. 1, a first light source 10 and a second light source 20 that are disposed such that their optical axes are perpendicular to each other, a dichroic mirror (light combining section) 40 that is disposed at the point of intersection of the optical axis of the first light source 10 and the optical axis of the second light source 20, and a light guide 43 that is disposed on the optical axis of the second light source 20.

Figure 3:
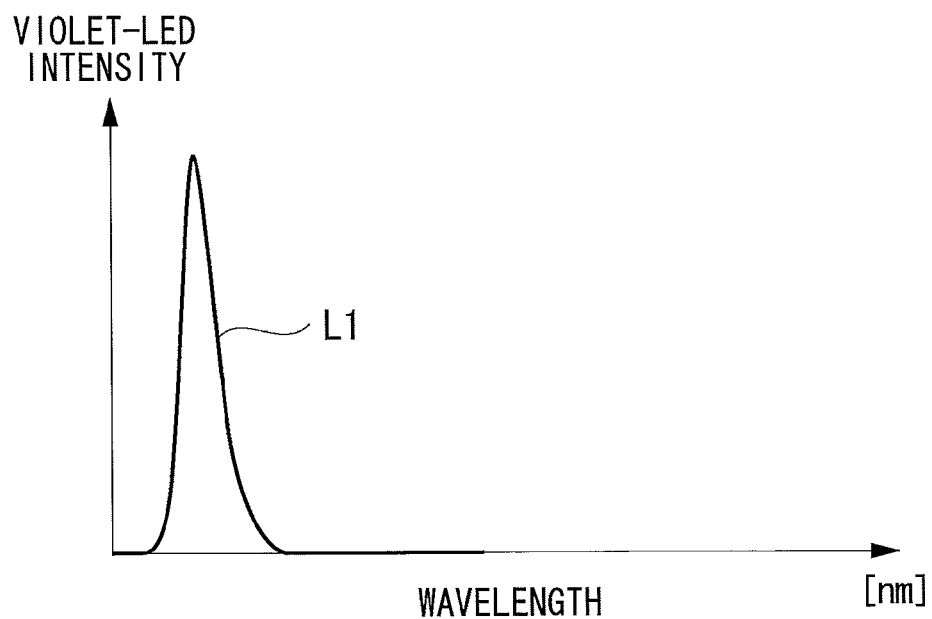
FIG. 3 is a graph showing a spectral characteristic of light from a first light source shown in FIG. 1.

The first light source 10 is an LED that emits light (first-wavelength-band light) L1 having relatively short wavelengths, such as violet light, as shown in FIG. 3.

Lens groups 11 and 12 that convert the light L1 from the first light source 10 into substantially collimated light are disposed on the axis of the light emitted from the first light source 10.

Figure 4:
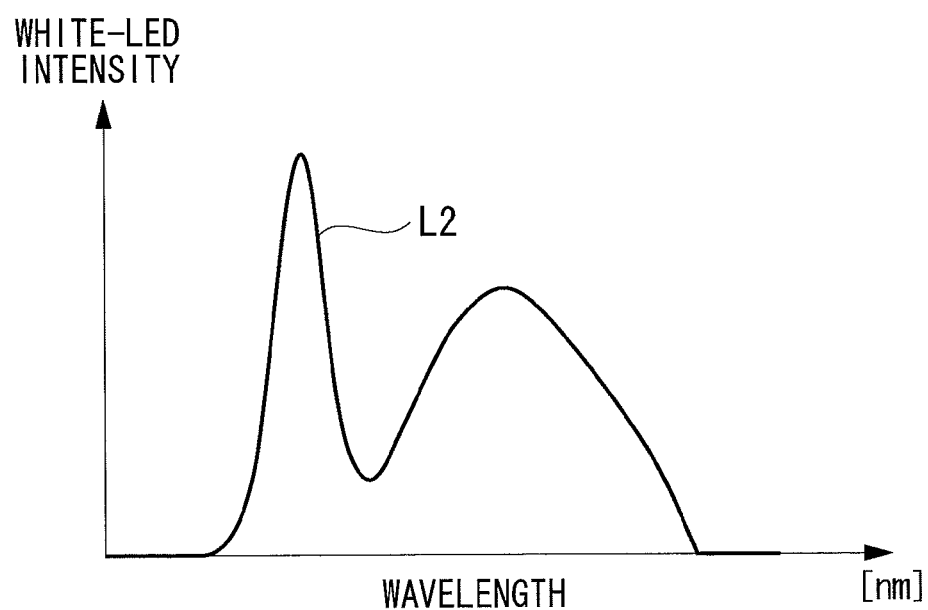
FIG. 4 is a graph showing a spectral characteristic of light from a second light source shown in FIG. 1.

The second light source 20 is an LED that emits light (second-wavelength-band light) L2 having a relatively broadband and continuous spectrum, such as white light, as shown in FIG. 4.

Lens groups 21 and 22 that convert the light L2 from the second light source 20 into substantially collimated light are disposed on the axis of the light emitted from the second light source 20.

Figure 2:
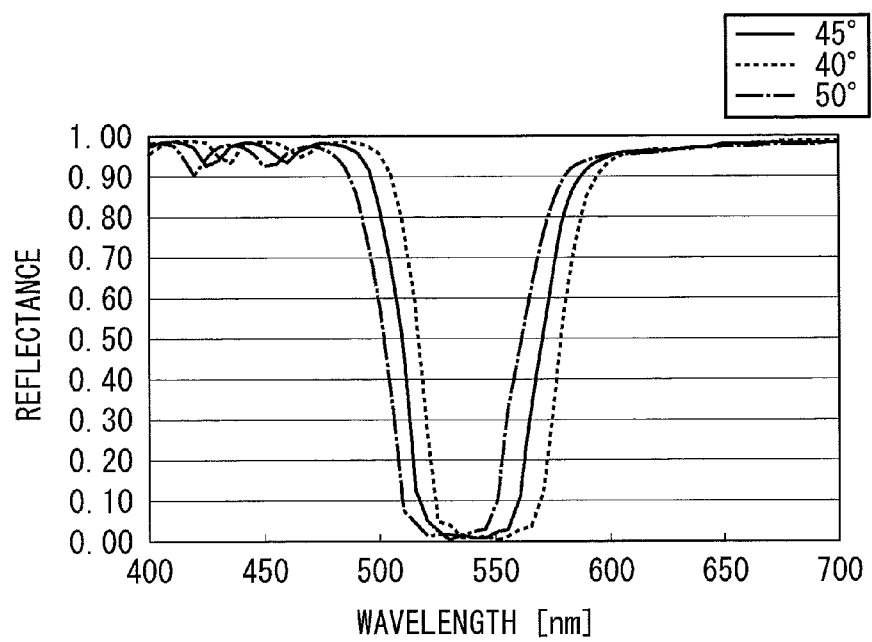
FIG. 2 is a graph showing a reflection characteristic of a dichroic mirror shown in FIG. 1.

As shown in FIG. 2, the dichroic mirror 40 has a reflection characteristic so as to transmit light having a wavelength band from 500 nm (inclusive) to 600 nm (exclusive) and reflect light having a wavelength band up to 500 nm (exclusive) and a wavelength band from 600 nm (inclusive), for example. Note that the graphs shown in the FIG. 2 indicate the angles of light incident on, the dichroic mirror 40.

With this reflection characteristic, the dichroic mirror 40 reflects the light L1 emitted from the first light source 10 and transmits, in the light L2 emitted from the second light source 20, light having a wavelength band from 500 nm (inclusive) to 600 nm (exclusive).

Figure 7:
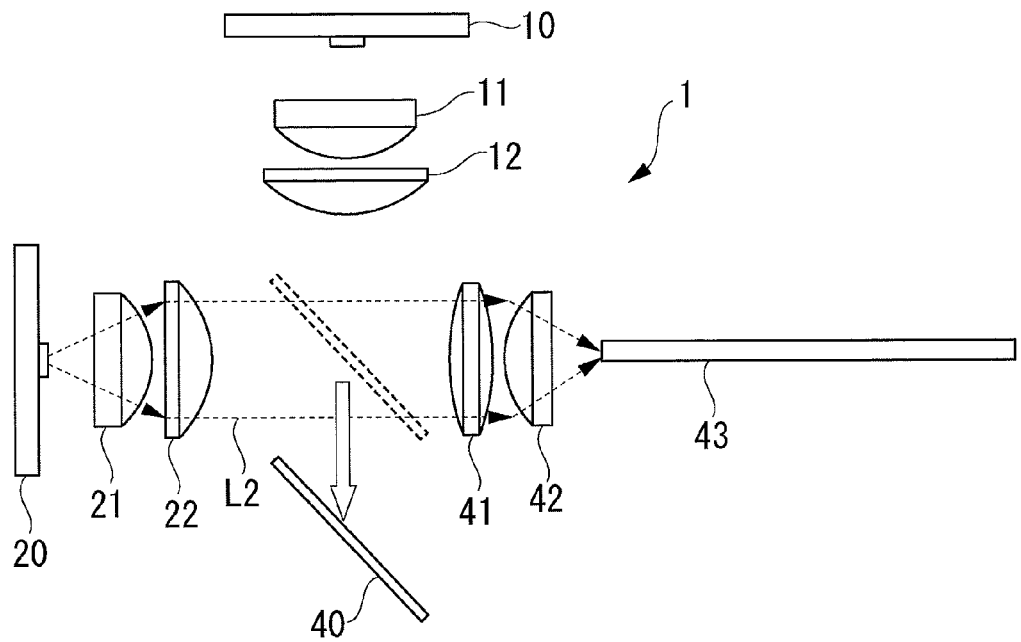
FIG. 7 is a view showing, in outline, the configuration of the illumination device shown in FIG. 1 in a WLI mode.

Furthermore, as shown in FIG. 7, the dichroic mirror 40 is moved in the direction of the optical axis of the first light source 10 by a movement mechanism (not shown) according to an illumination mode, to be described later, thereby being inserted into or removed from the optical axis of the second light source 20.

The illumination device 1 of this embodiment has an NBI (narrow band imaging) mode for radiating light having particular wavelength bands and a WLI (white light imaging) mode for radiating white light. When the user selects desired one of the illumination modes with a touch panel or a switch, for example, the dichroic mirror 40 is inserted into or removed from the optical axis of the second light source 20 by the movement mechanism (not shown).

In the NBI mode, light having two narrow wavelength bands (for example, light having a wavelength band from 390 to 445 nm and light having a wavelength band from 530 to 550 nm) that is easily absorbed into hemoglobin in the blood is radiated, so that capillaries in a superficial portion of a mucous membrane and mucosal fine patterns can be displayed in an emphasized manner.

In the WLI mode, white light having a broad wavelength band is radiated, so that observation with high color rendering properties can be performed.

Lens groups 41 and 42 that focus the light from the dichroic mirror 40 on an inlet end of the light guide 43 are disposed between the dichroic mirror 40 and the light guide 43.

The light guide 43 is a light guiding rod formed of glass, for example, and guides the light from the dichroic mirror 40 focused by the lens groups 41 and 42 to an outlet end thereof.

The operation of the illumination device 1, having the above-described configuration, will be described below.

First, in the NBI mode, the dichroic mirror 40 is disposed on the optical axis of the second light source 20, as shown in FIG. 1.

In this state, the first light source 10 and the second light source 20 are turned on.

The light L1 having relatively short wavelengths, such as violet light, is emitted from the first light source 10. The light L1 emitted from the first light source 10 is converted into substantially collimated light by the lens groups 11 and 12 and is reflected to the inlet end of the light guide 43 by the dichroic mirror 40.

Figure 5:
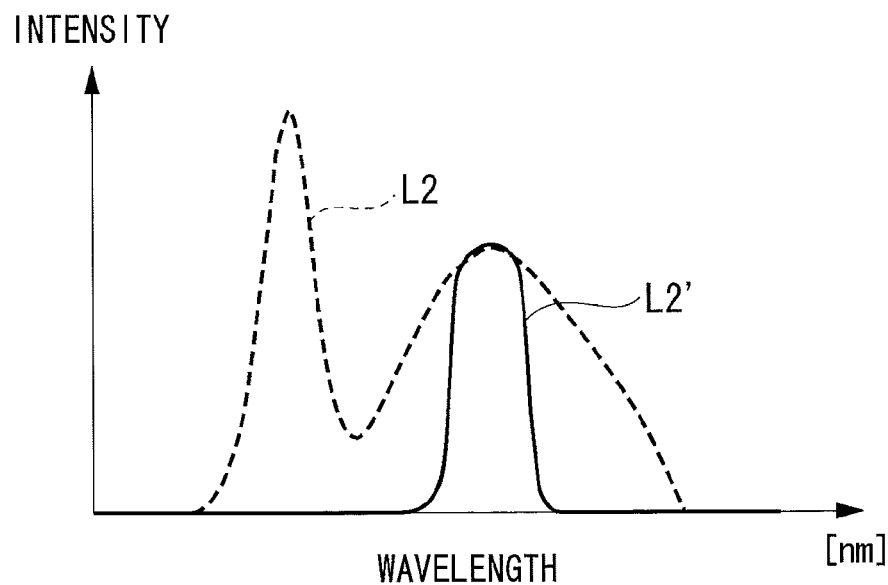
FIG. 5 is a graph showing a spectral characteristic of the light from the second light source after being transmitted through the dichroic mirror.

The light L2 having a relatively broadband and continuous spectrum, such as white light, is emitted from the second light source 20. The light L2 emitted from the second light source 20 is converted into substantially collimated light by the lens groups 21 and 22 and is incident on the dichroic mirror 40. At the dichroic mirror 40, part of the light L2 emitted from the second light source 20 is transmitted to the inlet end of the light guide 43, and the other part thereof is reflected, as shown in FIG. 5. Specifically, in the light L2 emitted from the second light source 20, the dichroic mirror 40 transmits light L2' having a wavelength band from 500 nm (inclusive) to 600 nm (exclusive) and reflects light having a wavelength band up to 500 nm (exclusive) and a wavelength band from 600 nm (inclusive), for example.

Figure 6:
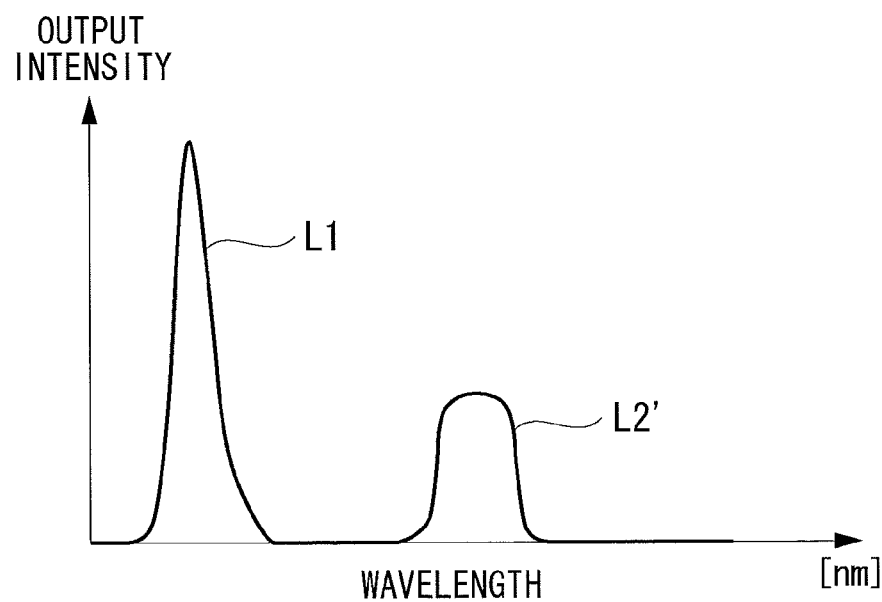
FIG. 6 is a graph showing a spectral characteristic of light output in the NBI mode.

The dichroic mirror 40, having this reflection characteristic, combines the light L1 emitted from the first light source 10 with the light L2' having a wavelength band from 500 nm (inclusive) to 600 nm (exclusive) in the light L2 emitted from the second light source 20, as shown in FIG. 6. The thus-combined light is focused on the inlet end of the light guide 43 by the lens groups 41 and 42, is guided by the light guide 43 to the outlet end thereof, and is output therefrom.

By doing so, it is possible to radiate light having two narrow wavelength bands that is easily absorbed into hemoglobin in the blood (for example, light having a wavelength band from 390 to 445 nm and light having a wavelength band from 530 to 550 nm) and to display capillaries in a superficial portion of the mucous membrane and mucosal fine patterns in an emphasized manner.

Next, in the WLI mode, the dichroic mirror 40 is moved in the direction of the optical axis of the first light source 10 by the movement mechanism (not shown), and is removed from the light path of the second light source 20, as shown in FIG. 7.

In this state, the second light source 20 is turned on. Note that the first light source 10 may also be turned on because light from the first light source 10 is not guided to the inlet end of the light guide 43 in this state.

The light L2 having a relatively broadband and continuous spectrum, such as white light, is emitted from the second light source 20. The light L2 emitted from the second light source 20 is converted into substantially collimated light by the lens groups 21 and 22, is focused on the inlet end of the light guide 43 by the lens groups 41 and 42, and is guided by the light guide 43 to the outlet end thereof.

Figure 8:
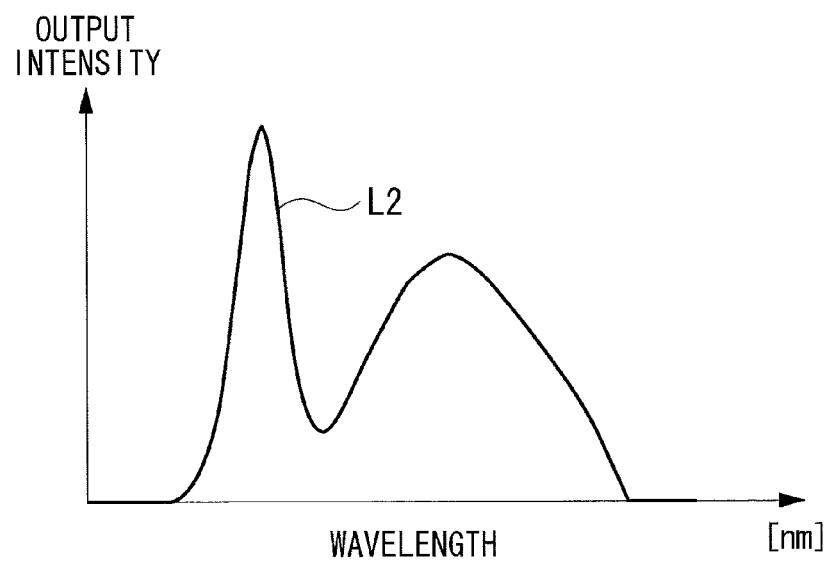
FIG. 8 is a graph showing a spectral characteristic of light output in the WLI mode.

Thus, it is possible to radiate the light L2 emitted from the second light source 20, i.e., white light having a broadband and continuous spectrum, as shown in FIG. 8, and to perform observation with high color rendering properties.

As described above, according to the illumination device 1 of this embodiment, the light L1 from the first light source 10 and the light L2 from the second light source 20 are combined by the dichroic mirror 40 and output. In this case, by moving the dichroic mirror 40 in the direction of the optical axis of the first light source 10 with the movement mechanism (not shown), it is possible to switch between and output light having different wavelength bands. By doing so, it is possible to output light by switching between the wavelength bands according to the subject to be illuminated.

More specifically, in order to output light having particular wavelength bands, the NBI mode is selected, and the first light source 10 and/or the second light source 20 are/is turned on with the dichroic mirror 40 disposed on the axis of the light L2. As a result, light having particular wavelength bands can be output. Furthermore, in order to output broad light, such as white light, the WLI mode is selected, and the second light source 20 is turned on with the dichroic mirror 40 removed from the optical axis of the second light source 20. As a result, the light L2 having a broadband and continuous spectrum can be output directly.

Second Embodiment

Next, an illumination device according to a second embodiment of the present invention will be described mainly with reference to FIGS. 9 to 17.

The illumination device of this embodiment differs from that of the first embodiment in that a third light source 30 is provided in addition to the first light source 10 and the second light source 20. The differences in the illumination device of this embodiment from the first embodiment will be mainly described below, and a description of similarities will be omitted.

Figure 9:
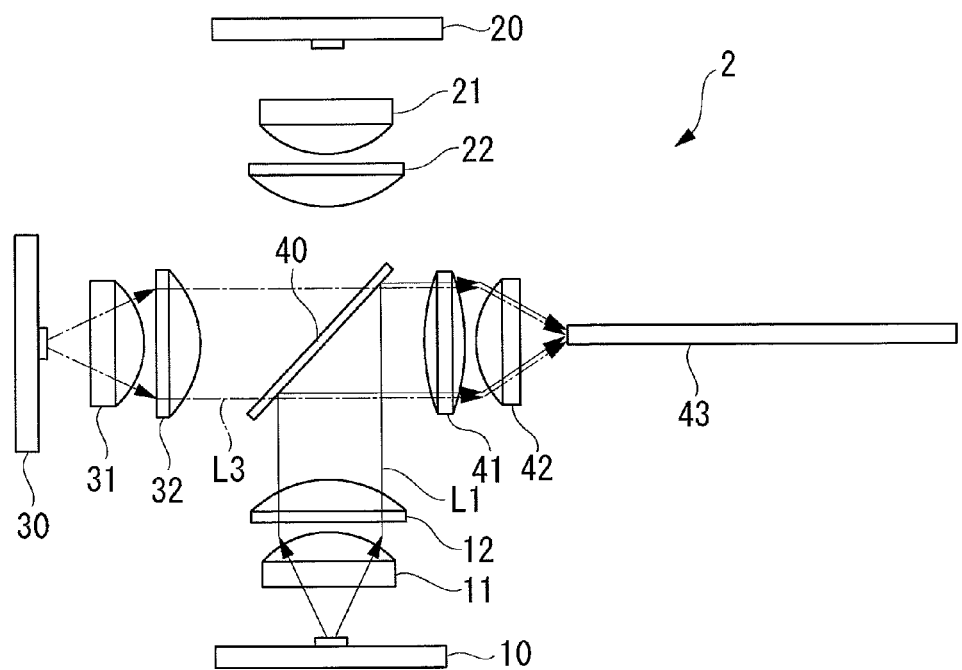
FIG. 9 is a view showing, in outline, the configuration of an illumination device according to a second embodiment of the present invention (NBI mode).

As shown in FIG. 9, an illumination device 2 of this embodiment includes the first light source 10, the second light source 20, and the third light source 30 that are disposed such that their optical axes are perpendicular to each other, the dichroic mirror (light combining section) 40 that is disposed at the point of intersection of the optical axes of the light sources, and the light guide 43 that is disposed on the optical axis of the third light source 30.

The first light source 10 and the second light source 20 are disposed facing each other, and the third light source 30 is disposed with the optical axis thereof directed in a direction that is perpendicular to the optical axes of the first light source 10 and the second light source 20.

Figure 11:
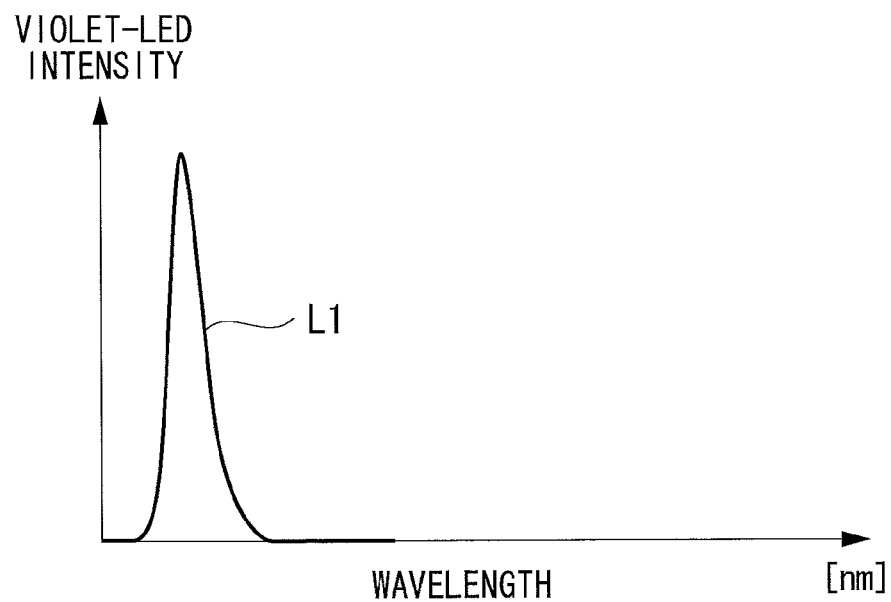
FIG. 11 is a graph showing a spectral characteristic of light from a first light source shown in FIG. 9.

The first light source 10 is an LED that emits light (first-wavelength-band light) L1 having relatively short wavelengths, such as violet light, as shown in FIG. 11.

The lens groups 11 and 12 that convert the light L1 from the first light source 10 into substantially collimated light are disposed on the axis of the light emitted from the first light source 10.

Figure 12:
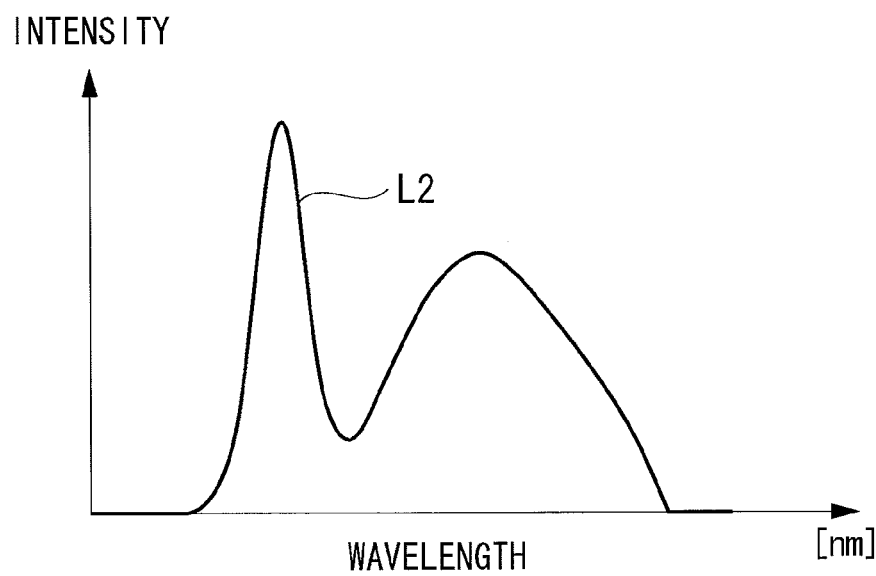
FIG. 12 is a graph showing a spectral characteristic of light from a second light source shown in FIG. 9.

The second light source 20 is an LED that emits light (second-wavelength-band light) L2 having a relatively broadband and continuous spectrum, such as white light, as shown in FIG. 12.

The lens groups 21 and 22 that convert the light L2 from the second light source 20 into substantially collimated light are disposed on the axis of the light emitted from the second light source 20.

Figure 13:
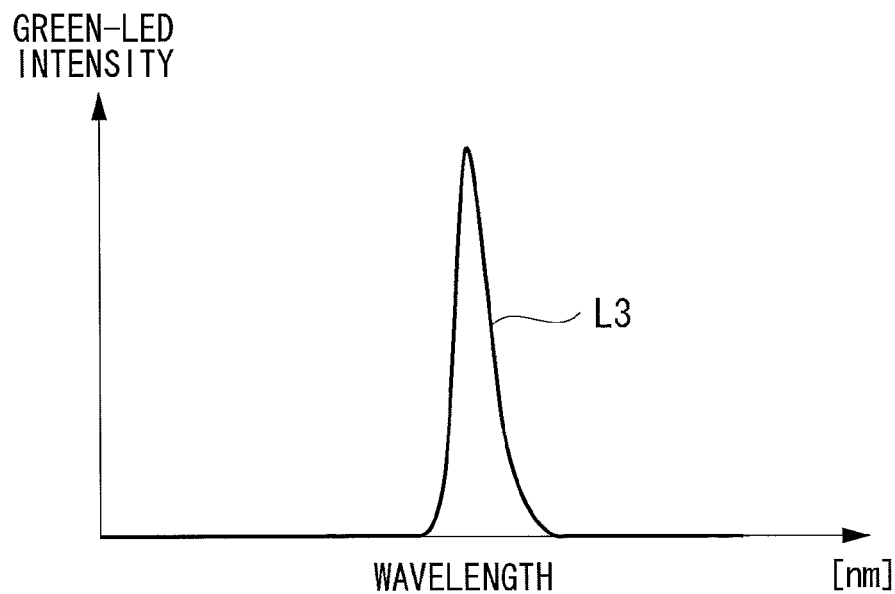
FIG. 13 is a graph showing a spectral characteristic of light from a third light source shown in FIG. 9.

The third light source 30 is an LED that emits light (third-wavelength-band light) L3 having intermediate wavelengths, such as green light, as shown in FIG. 13. The wavelength band of the light L3 is part of the wavelength band of the light L2 from the second light source 20.

Lens groups 31 and 32 that convert the light L3 from the third light source 30 into substantially collimated light are disposed on the axis of the light emitted from the third light source 30.

Figure 10:
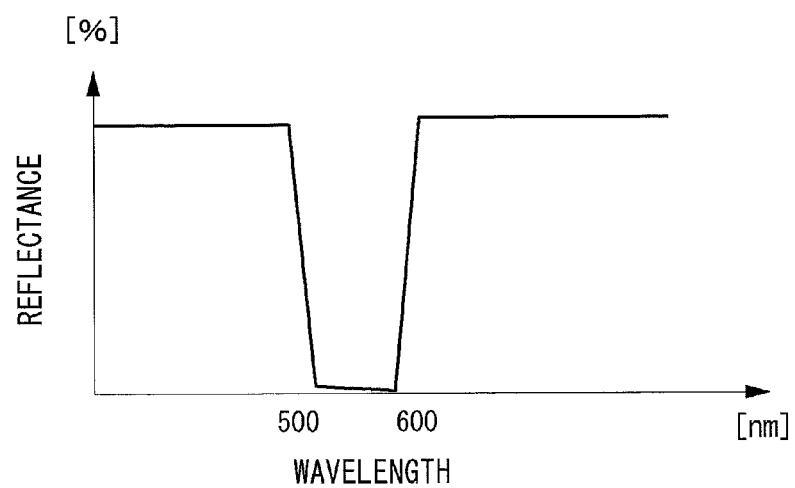
FIG. 10 is a graph showing a reflection characteristic of a dichroic mirror shown in FIG. 9.

As shown in FIG. 10, the dichroic mirror 40 has a reflection characteristic so as to transmit light having a wavelength band from 500 nm (inclusive) to 600 nm (exclusive) and reflect light having a wavelength band up to 500 nm (exclusive) and a wavelength band from 600 nm (inclusive), for example.

With this reflection characteristic, the dichroic mirror 40 reflects the light L1 emitted from the first light source 10, transmits light having a wavelength band from 500 nm (inclusive) to 600 nm (exclusive) in the light L2 emitted from the second light source 20, and transmits the light L3 emitted from the third light source 30.

Figure 15:
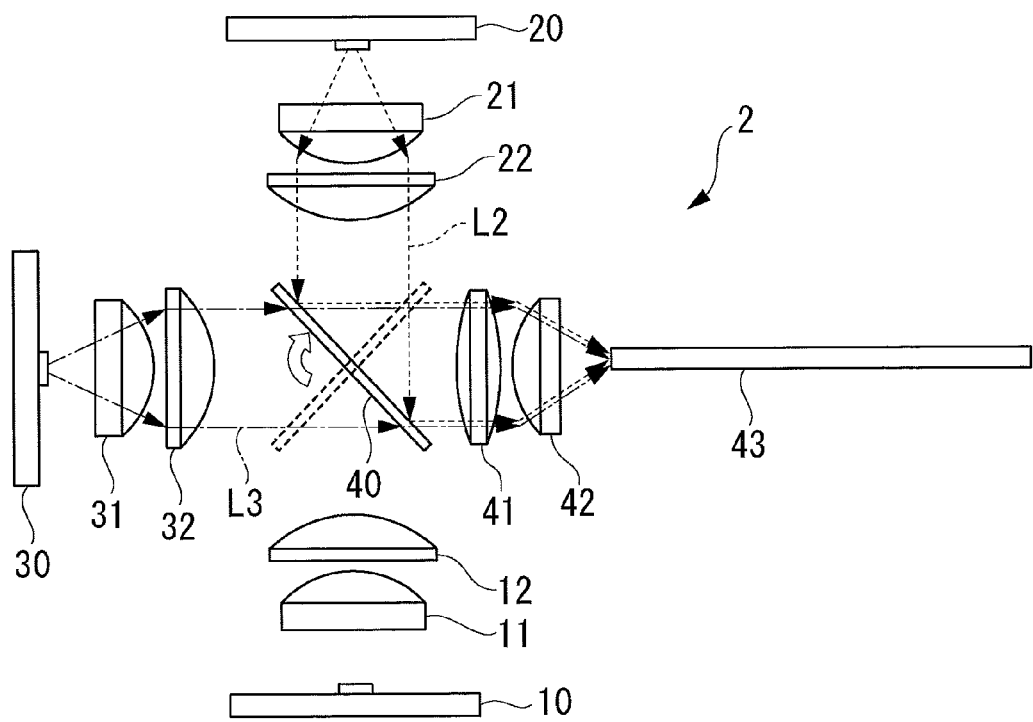
FIG. 15 is a view showing, in outline, the configuration of the illumination device shown in FIG. 9 in the WLI mode.

Furthermore, as shown in FIG. 15, the dichroic mirror 40 is rotated by a movement mechanism (not shown) about the axis perpendicular to the optical axes of the light sources (axis vertical to the figure), according to an illumination mode, to be described later.

The illumination device 2 of this embodiment has the NBI (narrow band imaging) mode for radiating light having particular wavelength bands and the WLI (white light imaging) mode for radiating white light. When the user selects desired one of the illumination modes with a touch panel or a switch, for example, the dichroic mirror 40 is rotated by the movement mechanism (not shown) about the axis perpendicular to the optical axes of the light sources.

The lens groups 41 and 42 that focus light from the dichroic mirror 40 on the inlet end of the light guide 43 are disposed between the dichroic mirror 40 and the light guide 43.

The light guide 43 is a light guiding rod formed of glass, for example, and guides the light from the dichroic mirror 40 focused by the lens groups 41 and 42 to the outlet end thereof.

The operation of the illumination device 2, having the above-described configuration, will be described below.

First, in the NBI mode, the dichroic mirror 40 is set at an angle so as to reflect the light L1 emitted from the first light source 10 to the inlet end of the light guide 43, as shown in FIG. 9.

In this state, the first light source 10 and the third light source 30 are turned on.

The light L1 having relatively short wavelengths, such as violet light, is emitted from the first light source 10. The light L1 emitted from the first light source 10 is converted into substantially collimated light by the lens groups 11 and 12 and is reflected to the inlet end of the light guide 43 by the dichroic mirror 40.

The light L3 having intermediate wavelengths, such as green light, is emitted from the third light source 30. The light L3 emitted from the third light source 30 is converted into substantially collimated light by the lens groups 31 and 32, is transmitted through the dichroic mirror 40, and enters the inlet end of the light guide 43.

Figure 14:
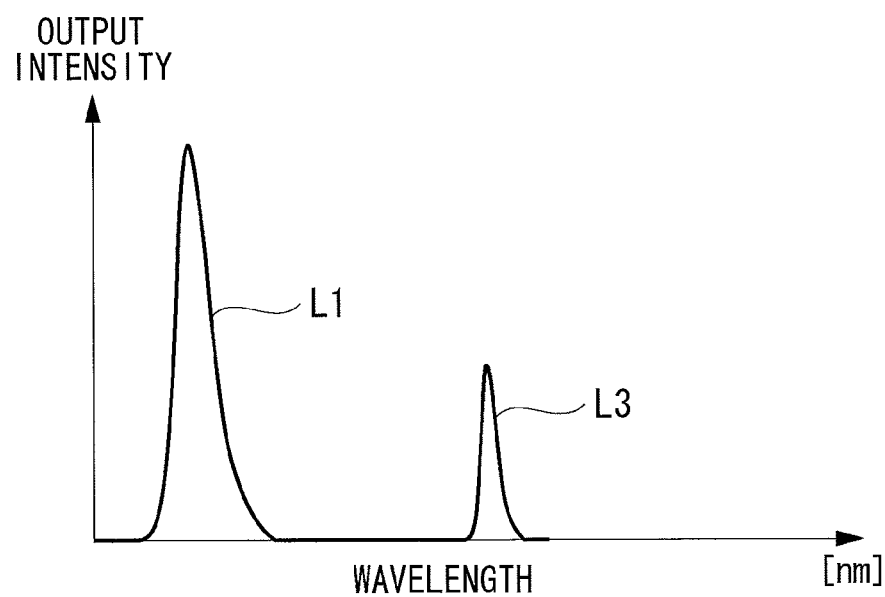
FIG. 14 is a graph showing a spectral characteristic of light output in the NBI mode.

The dichroic mirror 40, having this reflection characteristic, combines the light L1 emitted from the first light source 10 with the light L3 emitted from the third light source 30, as shown in FIG. 14. The thus-combined light is focused on the inlet end of the light guide 43 by the lens groups 41 and 42, is guided by the light guide 43 to the outlet end thereof, and is output therefrom.

By doing so, it is possible to radiate light having two narrow wavelength bands that is easily absorbed into hemoglobin in the blood (for example, light having a wavelength band from 390 to 445 nm and light having a wavelength band from 530 to 550 nm) and to display capillaries in a superficial portion of the mucous membrane and mucosal fine patterns in an emphasized manner.

Next, in the WLI mode, as shown in FIG. 15, the dichroic mirror 40 is rotated by the movement mechanism (not shown) about the axis perpendicular to the optical axes of the light sources and is set at an angle so as to reflect the light L2 emitted from the second light source 20 to the inlet end of the light guide 43.

In this state, the second light source 20 and the third light source 30 are turned on.

Figure 16:
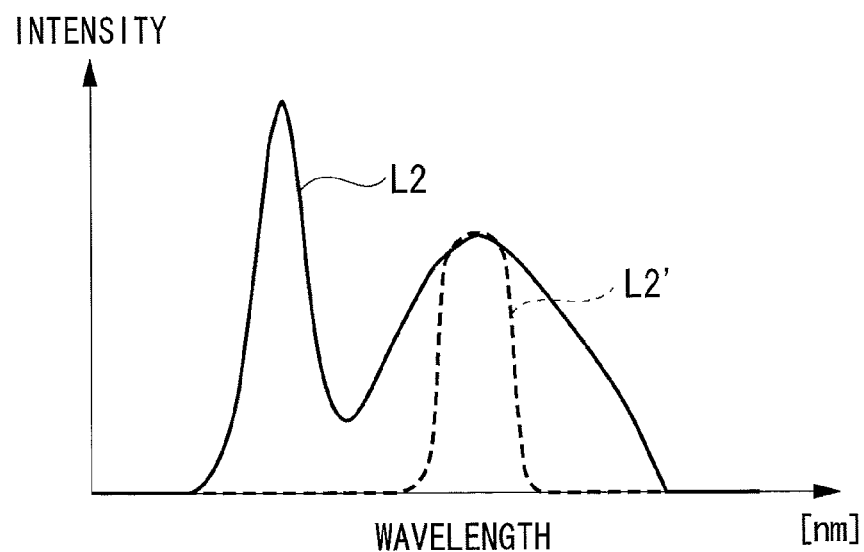
FIG. 16 is a graph showing a spectral characteristic of light from the second light source after being reflected by the dichroic mirror.

The light L2 having a relatively broadband and continuous spectrum, such as white light, is emitted from the second light source 20. The light L2 emitted from the second light source 20 is converted into substantially collimated light by the lens groups 21 and 22 and is incident on the dichroic mirror 40. At the dichroic mirror 40, part of the light L2 emitted from the second light source 20 is transmitted to the inlet end of the light guide 43, and the other part thereof is reflected, as shown in FIG. 16. Specifically, in the light L2 emitted from the second light source 20, the dichroic mirror 40 transmits light having a wavelength band from 500 nm (inclusive) to 600 nm (exclusive) and reflects light L2' having a wavelength band up to 500 nm (exclusive) and a wavelength band from 600 nm (inclusive), for example.

Figure 17:
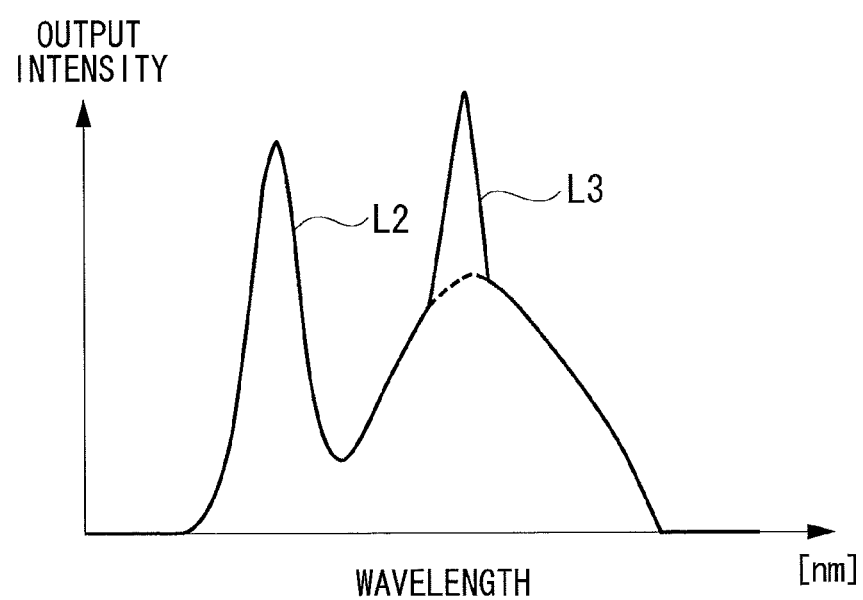
FIG. 17 is a graph showing a spectral characteristic of light output in the WLI mode.

The dichroic mirror 40, having this reflection characteristic, combines the light L3 emitted from the third light source 30 and the light having a wavelength band up to 500 nm (exclusive) and a wavelength band from 600 nm (inclusive) in the light L2 emitted from the second light source 20, as shown in FIG. 17. The thus-combined light is focused on the inlet end of the light guide 43 by the lens groups 41 and 42, is guided by the light guide 43 to the outlet end thereof, and is output therefrom.

As a result, the light L2' having a wavelength band from 500 nm (inclusive) to 600 nm (exclusive) in the light L2 emitted from the second light source 20 can be replaced with the light L3 emitted from the third light source 30, for output. It is known that, when the intensity of light having intermediate wavelengths, such as green light, is increased, the human eye perceives a significant increase in brightness. Therefore, the intensity of the light L3 from the third light source 30 is increased, thereby making it possible to radiate bright white light having a broadband and continuous spectrum and to improve the accuracy of observation.

As described above, according to the illumination device 2 of this embodiment, in order to output light having particular wavelength bands, the NBI mode is selected, and the dichroic mirror 40 is rotated about the axis perpendicular to the optical axes of the light sources so as to reflect the light L1 from the first light source 10 in the direction of the axis of combined light to be output. In this state, the first light source 10 and/or the third light source 30 are/is turned on, thus outputting light having particular wavelength bands.

Furthermore, in order to output broad light, such as white light, the WLI mode is selected, and the dichroic mirror 40 is rotated about the axis perpendicular to the optical axes of the light sources so as to reflect the light L2 from the second light source 20 in the direction of the axis of combined light to be output. In this state, the second light source 20 and the third light source 30 are turned on, thus outputting bright combined light that has a broadband and continuous spectrum and that is obtained after part of the wavelength band of the light L2 from the second light source 20 is replaced with that of the light L3 from the third light source 30.

Third Embodiment

Next, an illumination device according to a third embodiment of the present invention will be described mainly with reference to FIGS. 18 to 29.

The illumination device of this embodiment differs from those of the above-described embodiments in that an MI (molecular imaging) mode using IR light is provided in addition to the NBI mode and the WLI mode. The differences in the illumination device of this embodiment from those of the above-described embodiments will be mainly described below, and a description of similarities will be omitted.

The MI (molecular imaging) is an observation method in which the distribution and the movement of particular molecules (for example, glucose and various proteins) in the body are visualized with PET-CT etc. to dynamically capture various phenomena occurring in the body. With this observation method, the presence or absence of cancer, neurological disease, or heart disease, for example, the degree of progress thereof, and the degree of malignancy thereof can be diagnosed.

Figure 18:
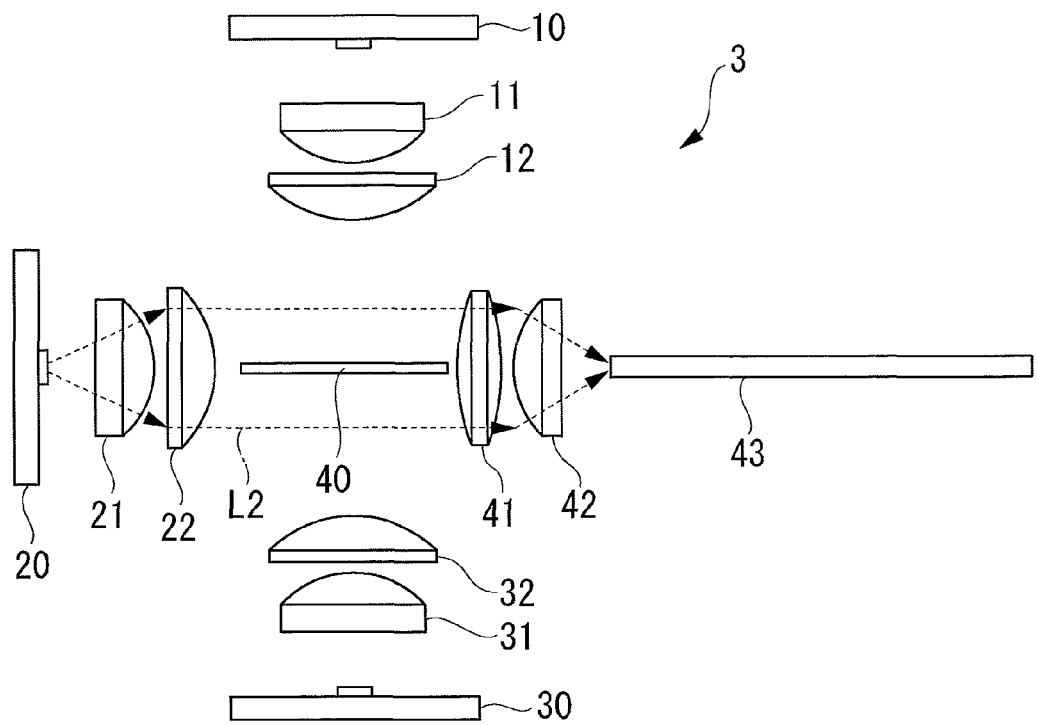
FIG. 18 is a view showing, in outline, the configuration of an illumination device according to a third embodiment of the present invention (WLI mode).

As shown in FIG. 18, an illumination device 3 of this embodiment includes the first light source 10, the second light source 20, and the third light source 30, which are disposed such that their optical axes are perpendicular to each other, the dichroic mirror (light combining section) 40, which is disposed at the point of intersection of the optical axes of the light sources, and the light guide 43 that is disposed on the optical axis of the second light source 20.

The first light source 10 and the third light source 30 are disposed facing each other, and the second light source 20 is disposed with the optical axis thereof directed in a direction that is perpendicular to the optical axes of the first light source 10 and the third light source 30.

Figure 20:
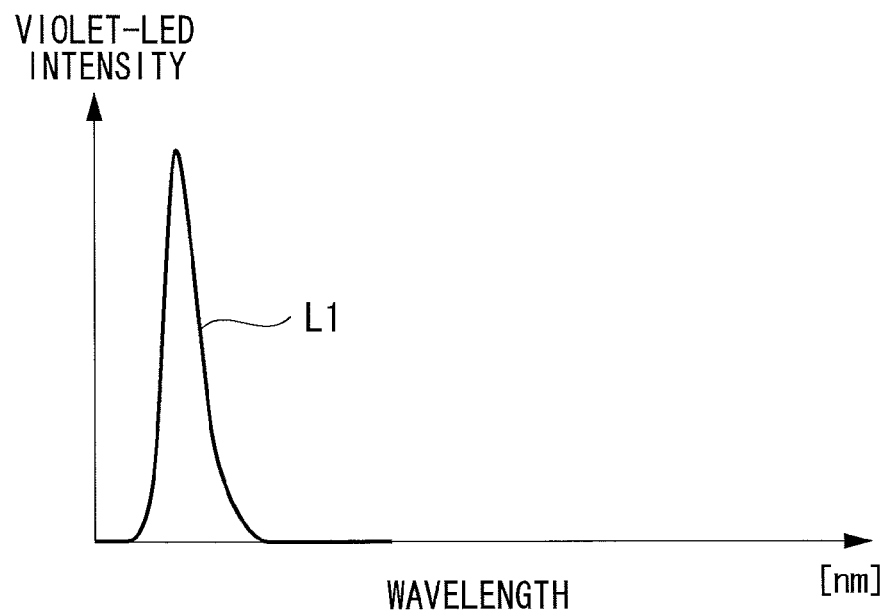
FIG. 20 is a graph showing a spectral characteristic of light from a first light source shown in FIG. 18.

The first light source 10 is an LED that emits light (first-wavelength-band light) L1 having relatively short wavelengths, such as violet light, as shown in FIG. 20.

The lens groups 11 and 12 that convert the light L1 from the first light source 10 into substantially collimated light are disposed on the axis of the light emitted from the first light source 10.

Figure 21:
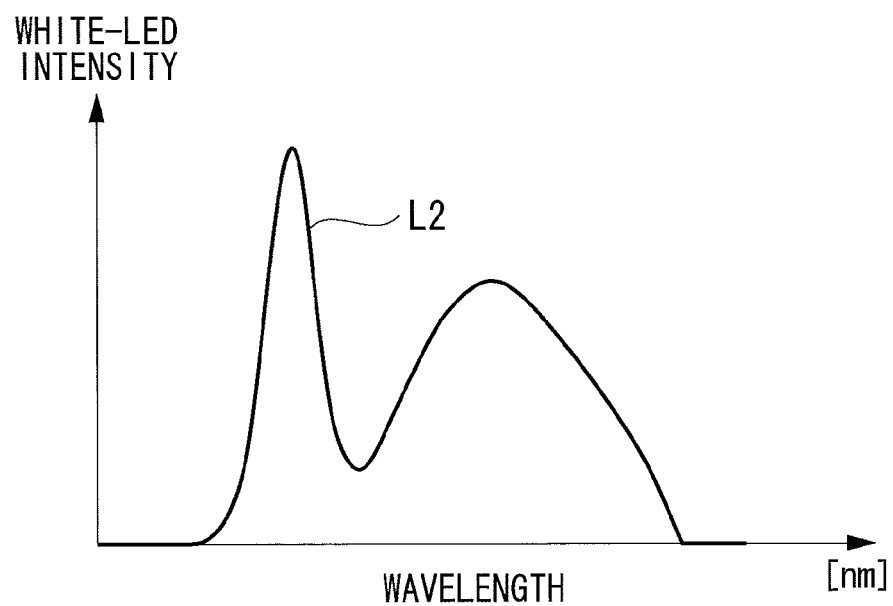
FIG. 21 is a graph showing a spectral characteristic of light from a second light source shown in FIG. 18.

The second light source 20 is an LED that emits light (second-wavelength-band light) L2 having a relatively broadband and continuous spectrum, such as white light, as shown in FIG. 21.

The lens groups 21 and 22 that convert the light L2 from the second light source 20 into substantially collimated light are disposed on the axis of the light emitted from the second light source 20.

Figure 22:
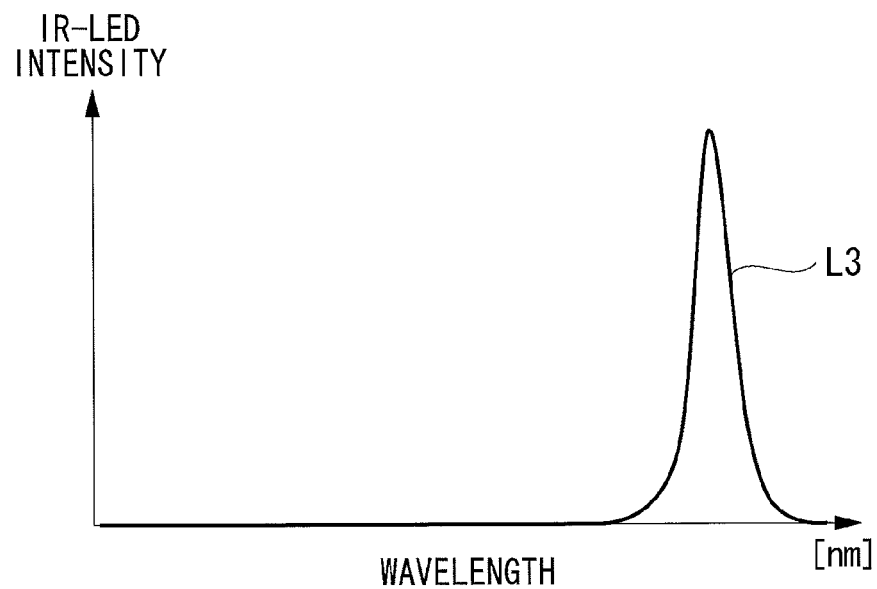
FIG. 22 is a graph showing a spectral characteristic of light from a third light source shown in FIG. 18.

The third light source 30 is an LED that emits IR light (third-wavelength-band light) L3, for example, as shown in FIG. 22. The light L3 has a wavelength band that is different from the light L2 from the second light source 20.

The lens groups 31 and 32 that convert the light L3 from the third light source 30 into substantially collimated light are disposed on the axis of the light emitted from the third light source 30.

Figure 19:
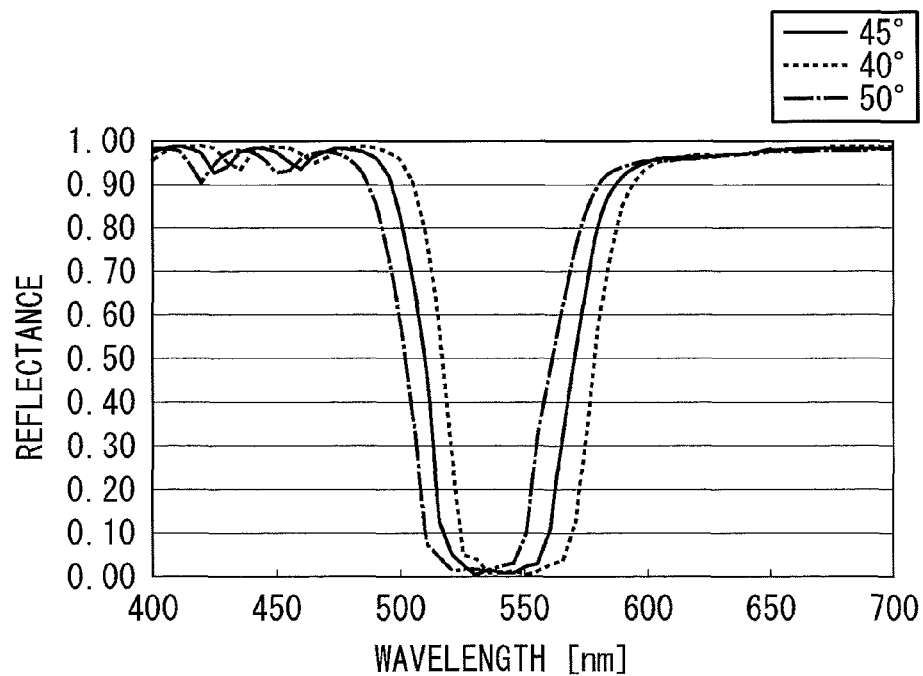
FIG. 19 is a graph showing a reflection characteristic of a dichroic mirror shown in FIG. 18.

As shown in FIG. 19, the dichroic mirror 40 has a reflection characteristic so as to transmit light having a wavelength band from 500 nm (inclusive) to 600 nm (exclusive) and reflect light having a wavelength band up to 500 nm (exclusive) and a wavelength band from 600 nm (inclusive), for example. Note that the graphs shown in the FIG. 19 indicate the angles of light incident on the dichroic mirror 40.

With this reflection characteristic, the dichroic mirror 40 reflects the light L1 emitted from the first light source 10, transmits light having a wavelength band from 500 nm (inclusive) to 600 nm (exclusive) in the light L2 emitted from the second light source 20, and transmits the light L3 emitted from the third light source 30.

Figure 24:
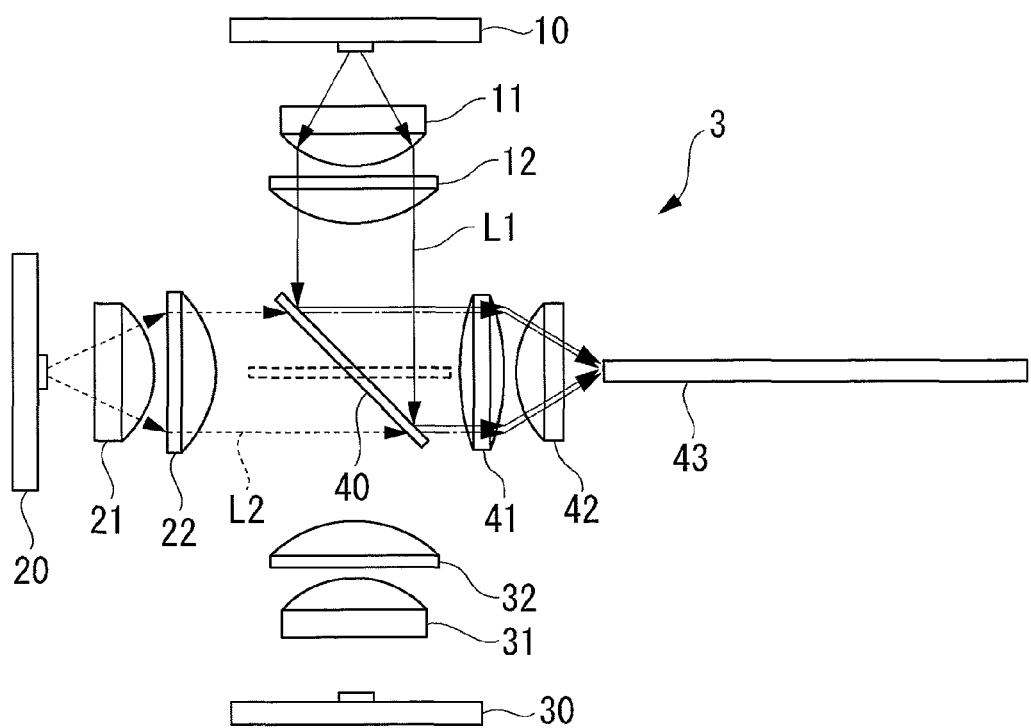
FIG. 24 is a view showing, in outline, the configuration of the illumination device shown in FIG. 18 in the NBI mode.

Furthermore, as shown in FIG. 24, the dichroic mirror 40 is rotated by a movement mechanism (not shown) about the axis perpendicular to the optical axes of the light sources (axis vertical to the figure), according to an illumination mode, to be described later.

The illumination device 3 of this embodiment has the NBI (narrow band imaging) mode for radiating light having particular wavelength bands, the WLI (white light imaging) mode for radiating white light, and the MI (molecular imaging) mode. When the user selects desired one of the illumination modes with a touch panel or a switch, for example, the dichroic mirror 40 is rotated by the movement mechanism (not shown) about the axis perpendicular to the optical axes of the light sources.

The lens groups 41 and 42 that focus light from the dichroic mirror 40 on the inlet end of the light guide 43 are disposed between the dichroic mirror 40 and the light guide 43.

The light guide 43 is a light guiding rod formed of glass, for example, and guides the light from the dichroic mirror 40 focused by the lens groups 41 and 42 to the outlet end thereof.

The operation of the illumination device 3, having the above-described configuration, will be described below.

First, in the WLI mode, the dichroic mirror 40 is rotated by the movement mechanism (not shown) about the axis perpendicular to the optical axes of the light sources, as shown in FIG. 18, and is disposed such that the reflecting surface thereof is in the direction of the optical axis of the second light source 20.

In this state, the second light source 20 is turned on.

The light L2 having a relatively broadband and continuous spectrum, such as white light, is emitted from the second light source 20. The light L2 emitted from the second light source 20 is converted into substantially collimated light by the lens groups 21 and 22, is focused on the inlet end of the light guide 43 by the lens groups 41 and 42, is guided by the light guide 43 to the outlet end thereof, and is output therefrom.

Figure 23:
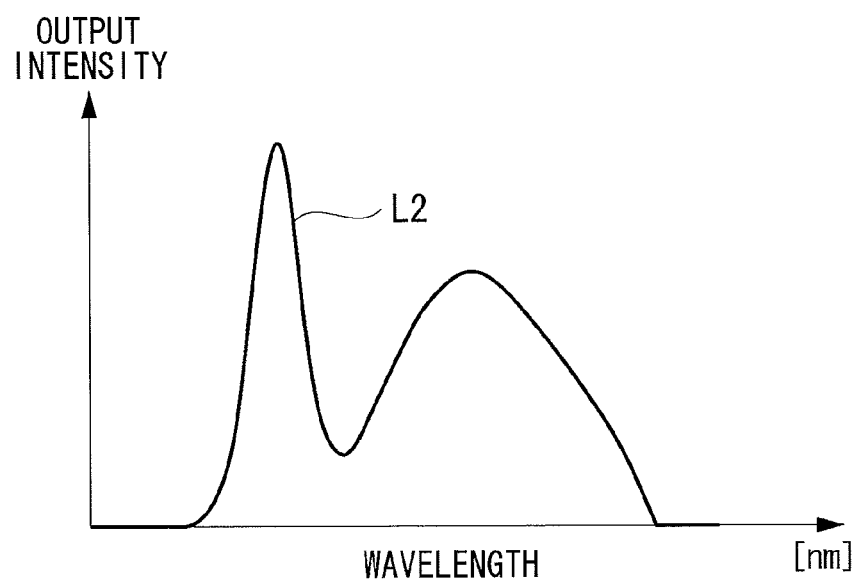
FIG. 23 is a graph showing a spectral characteristic of light output in the WLI mode.

Thus, it is possible to radiate the light L2 emitted from the second light source 20, i.e., white light having a broadband and continuous spectrum, as shown in FIG. 23, and to perform observation with high color rendering properties.

Next, in the NBI mode, the dichroic mirror 40 is set at an angle so as to reflect the light L1 emitted from the first light source 10 to the inlet end of the light guide 43, as shown in FIG. 24.

In this state, the first light source 10 and the second light source 20 are turned on.

The light L1 having relatively short wavelengths, such as violet light, is emitted from the first light source 10. The light L1 emitted from the first light source 10 is converted into substantially collimated light by the lens groups 11 and 12 and is reflected to the inlet end of the light guide 43 by the dichroic mirror 40.

Figure 25:
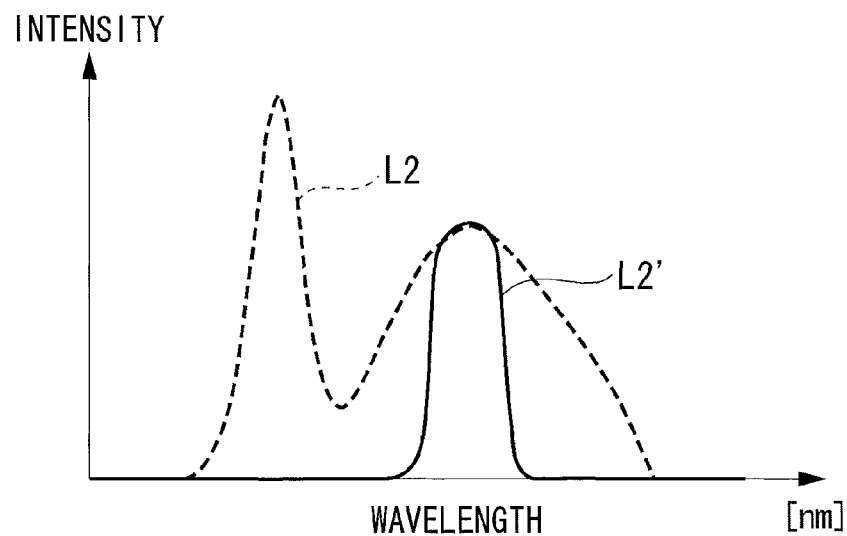
FIG. 25 is a graph showing a spectral characteristic of light from the second light source after being transmitted through the dichroic mirror.

The light L2 having a relatively broadband and continuous spectrum, such as white light, is emitted from the second light source 20. The light L2 emitted from the second light source 20 is converted into substantially collimated light by the lens groups 21 and 22 and is incident on the dichroic mirror 40. At the dichroic mirror 40, part of the light L2 emitted from the second light source 20 is transmitted to the inlet end of the light guide 43, and the other part thereof is reflected, as shown in FIG. 25. Specifically, in the light L2 emitted from the second light source 20, the dichroic mirror 40 transmits the light L2' having a wavelength band from 500 nm (inclusive) to 600 nm (exclusive) and reflects light having a wavelength band up to 500 nm (exclusive) and a wavelength band from 600 nm (inclusive), for example.

Figure 26:
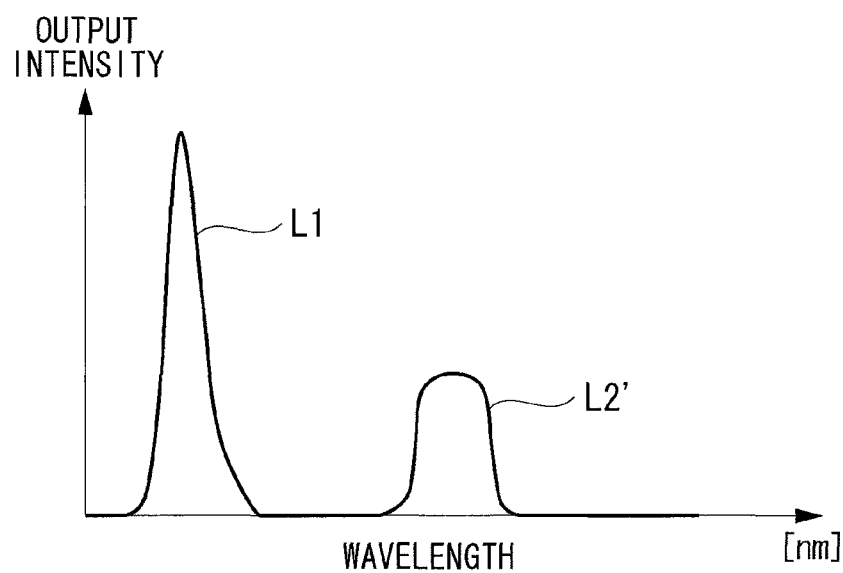
FIG. 26 is a graph showing a spectral characteristic of light output in the NBI mode.

The dichroic mirror 40, having this reflection characteristic, combines the light L1 emitted from the first light source 10 with the light L2' having a wavelength band from 500 nm (inclusive) to 600 nm (exclusive) in the light L2 emitted from the second light source 20, as shown in FIG. 26. The thus-combined light is focused on the inlet end of the light guide 43 by the lens groups 41 and 42, is guided by the light guide 43 to the outlet end thereof, and is output therefrom.

By doing so, it is possible to radiate light having two narrow wavelength bands that is easily absorbed into hemoglobin in the blood (for example, light having a wavelength band from 390 to 445 nm and light having a wavelength band from 530 to 550 nm) and to display capillaries in a superficial portion of the mucous membrane and mucosal fine patterns in an emphasized manner.

Figure 27:
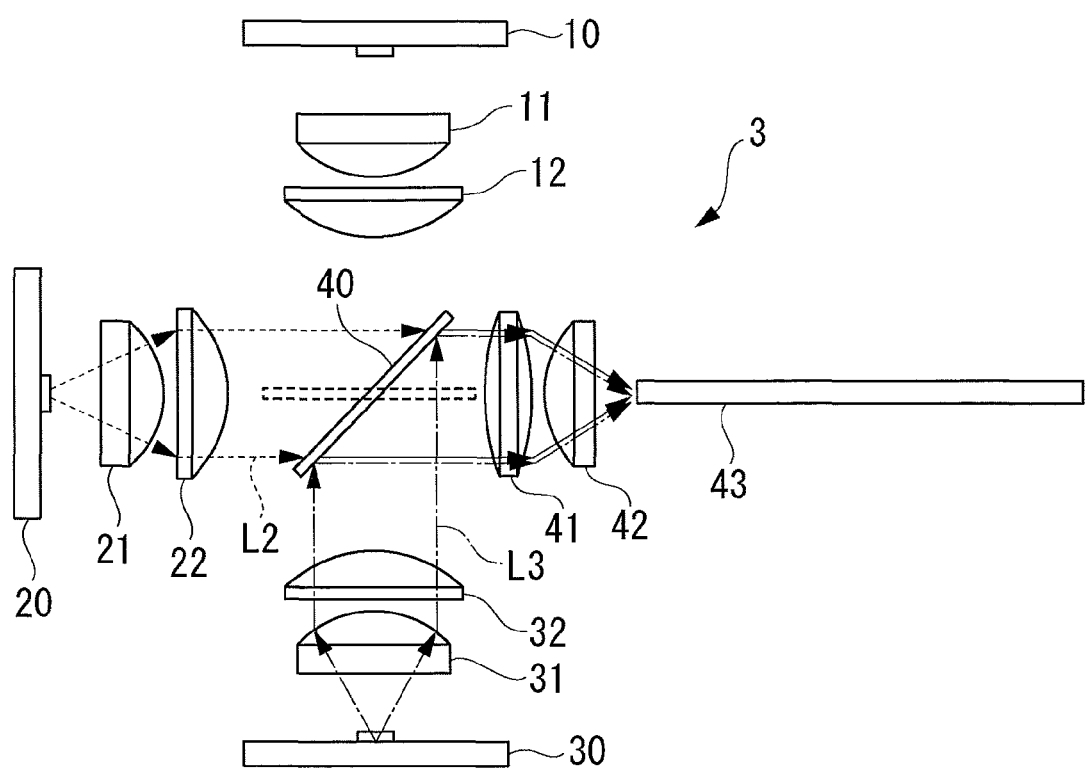
FIG. 27 is a view showing, in outline, the configuration of the illumination device shown in FIG. 18 in an MI mode.

Next, in the MI mode, the dichroic mirror 40 is set at an angle so as to reflect the light L3 emitted from the third light source 30 to the inlet end of the light guide 43, as shown in FIG. 27.

In this state, the second light source 20 and the third light source 30 are turned on.

The light L3 having relatively short wavelengths, such as IR light, is emitted from the third light source 30. The light L3 emitted from the third light source 30 is converted into substantially collimated light by the lens groups 31 and 32 and is reflected by the dichroic mirror 40 to the inlet end of the light guide 43.

Figure 28:
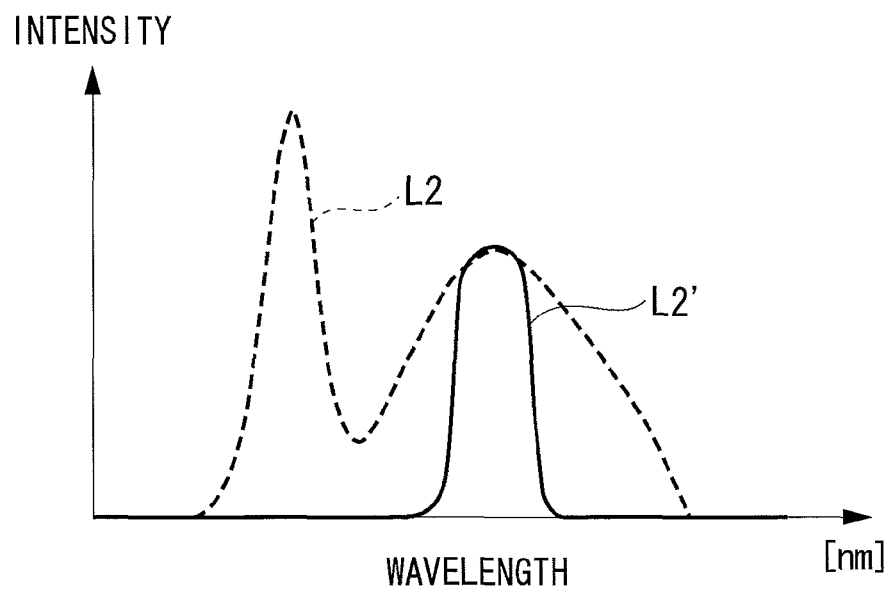
FIG. 28 is a graph showing a spectral characteristic of light from the second light source after being transmitted through the dichroic mirror.

The light L2 having a relatively broadband and continuous spectrum, such as white light, is emitted from the second light source 20. The light L2 emitted from the second light source 20 is converted into substantially collimated light by the lens groups 21 and 22 and is incident on the dichroic mirror 40. At the dichroic mirror 40, part of the light L2 emitted from the second light source 20 is transmitted to the inlet end of the light guide 43, and the other part thereof is reflected, as shown in FIG. 28. Specifically, in the light L2 emitted from the second light source 20, the dichroic mirror 40 transmits the light L2' having a wavelength band from 500 nm (inclusive) to 600 nm (exclusive) and reflects light having a wavelength band up to 500 nm (exclusive) and a wavelength band from 600 nm (inclusive), for example.

Figure 29:
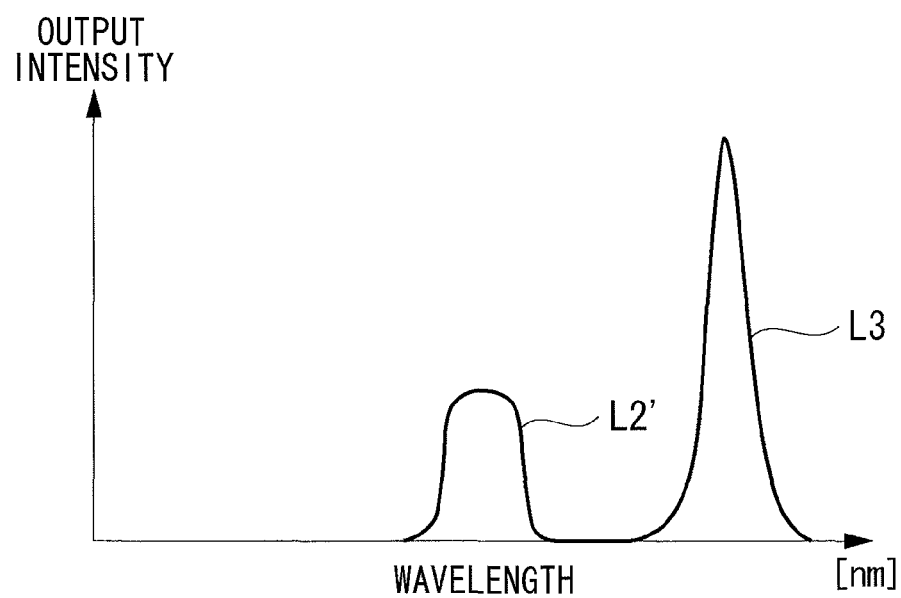
FIG. 29 is a graph showing a spectral characteristic of light output in the MI mode.

The dichroic mirror 40, having this reflection characteristic, combines the light L3 emitted from the third light source 30 and the light L2' having a wavelength band from 500 nm (inclusive) to 600 nm (exclusive) in the light L2 emitted from the second light source 20, as shown in FIG. 29. The thus-combined light is focused on the inlet end of the light guide 43 by the lens groups 41 and 42, is guided by the light guide 43 to the outlet end thereof, and is output therefrom.

Thus, by using the light L3 emitted from the third light source 30 as excitation light and using the light L2' having a wavelength band from 500 nm (inclusive) to 600 nm (exclusive) in the light L2 emitted from the second light source 20 as reference light, it is possible to observe the distribution and the movement of particular molecules (for example, glucose and various proteins) in the body and to diagnose the presence or absence of cancer, neurological disease, or heart disease, for example, the degree of progress thereof, and the degree of malignancy thereof.

As described above, according to the illumination device 3 of this embodiment, in order to output light having particular wavelength bands that includes the light L1 from the first light source 10, the NBI mode is selected, and the dichroic mirror 40 is rotated about the axis perpendicular to the optical axes of the light sources so as to reflect the light L1 from the first light source 10 in the direction of the axis of combined light to be output. In this state, the first light source 10 and/or the second light source 20 are/is turned on, thus outputting light having desired wavelength bands.

Furthermore, for example, in order to output broad light, such as white light, the WLI mode is selected, and the dichroic mirror 40 is rotated about the axis perpendicular to the optical axes of the light sources such that the reflecting surface of the dichroic mirror 40, which is a plate-like filter, is in the direction of the optical axis of the second light source 20. In this state, the second light source 20 is turned on, thus outputting the light L2 having a broadband and continuous spectrum directly, without being reflected by the dichroic mirror 40.

Furthermore, in order to output light having particular wavelength bands that includes the light L3 (IR light) from the third light source 30, the MI mode is selected, and the dichroic mirror 40 is rotated about the axis perpendicular to the optical axes of the light sources so as to reflect the light L3 from the third light source 30 in the direction of the axis of combined light to be output. In this state, the third light source 30 and/or the second light source 20 are/is turned on, thus outputting light having desired wavelength bands.

First Modification

Figure 30:
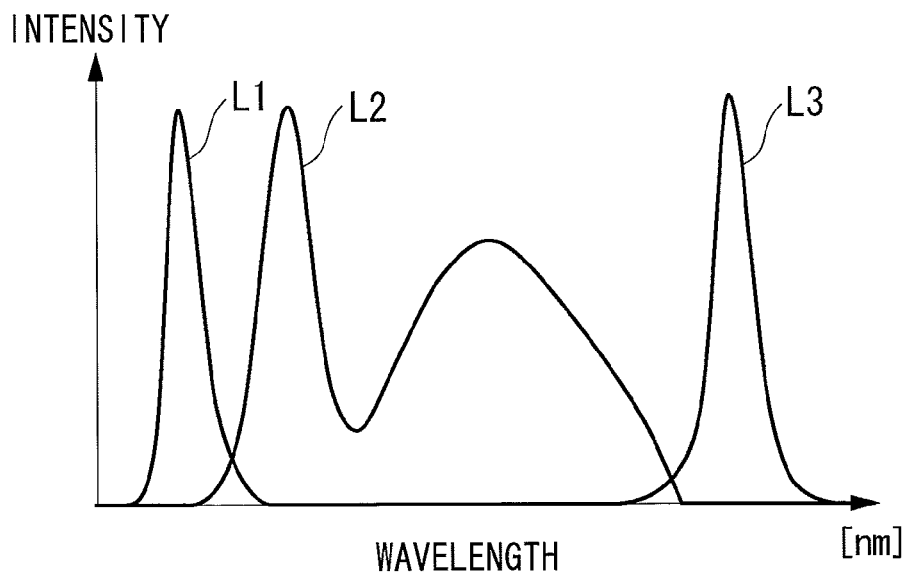
FIG. 30 is a graph showing a spectral characteristic of light superimposed in an illumination device according to a first modification.

In a first modification of the illumination device 3 of this embodiment, rotation of the dichroic mirror 40 and lighting of the light sources may be synchronized. The light L1 emitted from the first light source 10, the light L2 emitted from the second light source 20, and the light L3 emitted from the third light source 30 have a complementary relationship in terms of their spectra. Therefore, when the light sources are sequentially turned on in synchronization with rotation of the dichroic mirror 40, it is possible to output light having a broadband and continuous spectrum, as superimposed light, as shown in FIG. 30.

Furthermore, since the WLI mode, the NBI mode, and the MI mode can be sequentially switched at high speed, high-speed frame-sequential illumination can be performed. In this case, since images of a subject can be acquired in the three illumination modes by synchronizing the illumination modes with image acquisition, it is possible to superimpose the images obtained in the NBI mode and the MI mode on the image obtained in the WLI mode through image processing or to display the images while switching between them at high speed.

Second Modification

In a second modification of the illumination device 3 of this embodiment, the stop angle of the dichroic mirror 40 may be fine-tuned.

Specifically, by taking account of the incidence angle dependence (wavelength shift) of the dichroic mirror 40, the stop angle of the dichroic mirror 40 may be set to 43° and 40°, for example, in addition to the above-described three patterns, i.e., 45°, 0°, and −45°. Thus, wavelengths in the G band to be extracted from white light (the light L2 emitted from the second light source 20) can be desirably set according to the angle at which the dichroic mirror 40 is stopped.

For example, violet light and green light are used in both the NBI mode and an AFI mode, but the wavelengths of light to be radiated are slightly different therebetween (the center wavelength of the G band in the NBI mode is 10 nm shorter than that in the AFI mode). By changing the stop angle of the filter between the NBI mode and the AFI mode, the optimum wavelengths in the G band can be provided.

Figure 31:
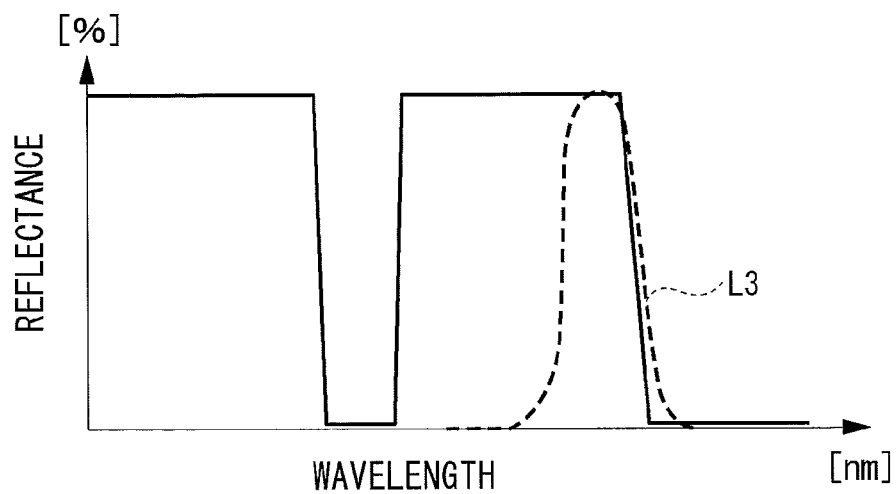
FIG. 31 is a graph showing a reflection characteristic of a dichroic mirror of an illumination device according to a second modification.
Figure 32:
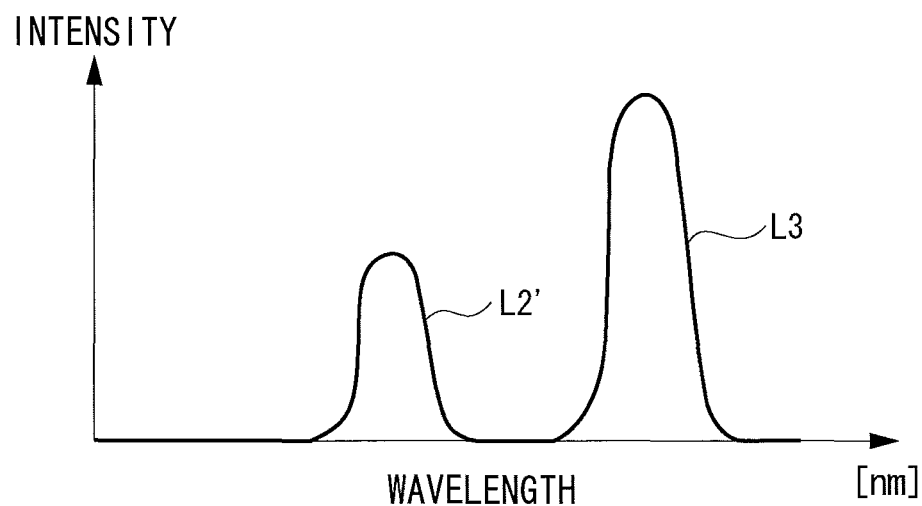
FIG. 32 is a graph showing a spectral characteristic of light combined by the dichroic mirror of FIG. 31.
Figure 33:
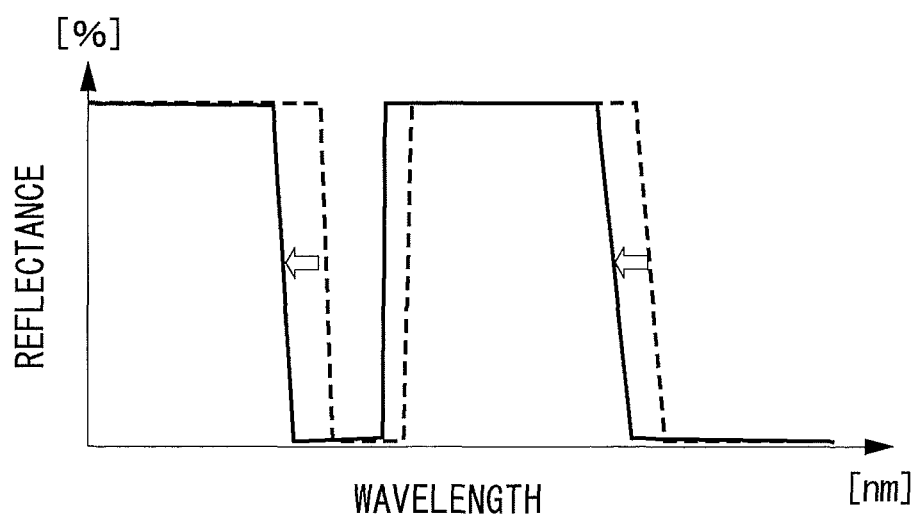
FIG. 33 is a graph showing a reflection characteristic when the stop angle of the dichroic mirror of FIG. 31 is changed.
Figure 34:
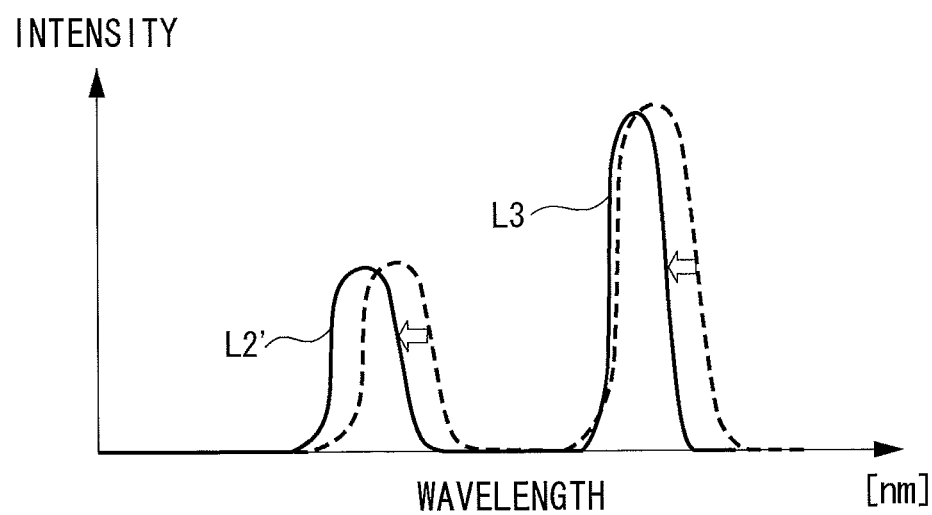
FIG. 34 is a graph showing a spectral characteristic of light combined by the dichroic mirror of FIG. 33.

Furthermore, when the spectral characteristic of the dichroic mirror 40 is set as shown in FIG. 31, and the stop angle of the dichroic mirror 40 is changed as shown in FIG. 33, the wavelengths of light from the light sources can be shifted as shown in FIG. 32 and FIG. 34. As a result, for example, even in order to shift the wavelengths of excitation light by several tens of nanometers depending on the type of fluorescent reagent, the stop angle of the dichroic mirror 40 can be changed to fine-tune the wavelengths of excitation light (output light), for fluoroscopy.

The embodiments of the present invention have been described above in detail with reference to the drawings; however, the specific configurations are not limited to the embodiments, and design changes that do not depart from the scope of the present invention are also encompassed. For example, the present invention can be applied to an embodiment obtained by appropriately combining the above-described embodiments and modifications.

Furthermore, in each of the embodiments, a description has been given of an example case in which the illumination device of the present invention is applied to the observation system. Example systems to which such an illumination device can be applied include an endoscope system using special light (as in infrared-light observation and drug fluorescence observation) and a microscope system for fluoroscopy.

Furthermore, in the embodiments, a description has been given of a case where each light source is a single separate LED; however, a multi-chip LED module in which chips having different wavelengths are packaged may be used. As a result, it is possible to increase the options for the spectrum of output light (combined light) and to obtain light of an intended band.

Furthermore, although a description has been given of a case where the dichroic mirror is used as a specific example of the light combining section, for example, a dichroic prism may be used.

REFERENCE SIGNS LIST

1, 2, 3 illumination device
10 first light source
11, 12 lens group
20 second light source
21, 22 lens group
30 third light source
31, 32 lens group
40 dichroic mirror (light combining section)
41, 42 lens group
43 light guide
L1 first-wavelength-band light
L2 second-wavelength-band light L3 third-wavelength-band light

The invention claimed is:

1. An illumination device comprising:
a first light source that emits first-wavelength-band light having a first wavelength band of violet color;
a second light source that emits second-wavelength-band light having a second wavelength band that is broader than the first wavelength band and having a continuous spectrum;
a light combining section that is composed of a dichroic mirror and that combines the first-wavelength-band light and the second-wavelength-band light; and
a combination-ratio adjusting section that adjusts the combination ratio of the first-wavelength-band light and the second-wavelength-band light to be combined by the light combining section.

2. The illumination device according to claim 1,
wherein the light combining section reflects the first-wavelength-band light, transmits part of the second-wavelength-band light, and combines the first-wavelength-band light and the second-wavelength-band light; and
the combination-ratio adjusting section inserts and removes the light combining section into and from the optical axis of the second light source.

3. The illumination device according to claim 1, further comprising a third light source that emits third-wavelength-band light having a third wavelength band that is part of the second wavelength band,
wherein the light combining section reflects the first-wavelength-band light and the second-wavelength-band light and transmits the third-wavelength-band light; and
the combination-ratio adjusting section rotates the light combining section about an axis perpendicular to the optical axes of the light sources.

4. The illumination device according to claim 1, further comprising a third light source that emits third-wavelength-band light having a third wavelength band that is different from the first wavelength band and the second wavelength band,
wherein the light combining section is a plate-like filter that reflects the first-wavelength-band light and the third-wavelength-band light and transmits part of the second-wavelength-band light; and
the combination-ratio adjusting section rotates the light combining section about an axis perpendicular to the optical axes of the light sources.

5. The illumination device according to claim 4, wherein the light sources are turned on in synchronization with rotation of the light combining section.

6. The illumination device according to claim 3, wherein the combination-ratio adjusting section fine-tunes the angle of rotation of the light combining section about the axis perpendicular to the optical axes of the light sources according to the wavelength band of light to be output.

7. An observation system comprising:
the illumination device according to claim 1; and
an imaging device that acquires an image of a specimen illuminated by the illumination device.

* * * * *